US007588905B2

(12) United States Patent
Ahearn et al.

(10) Patent No.: US 7,588,905 B2
(45) Date of Patent: *Sep. 15, 2009

(54) IDENTIFICATION AND MONITORING OF SYSTEMIC LUPUS ERYTHEMATOSUS

(75) Inventors: Joseph M. Ahearn, Sewickley, PA (US); Susan M. Manzi, Wexford, PA (US); Jeannine Navratil, Pittsburgh, PA (US)

(73) Assignee: University of Pittsburgh - Of the Commonwealth System of Higher Education, Pittsburgh, PA (US)

( * ) Notice: Subject to any disclaimer, the term of this patent is extended or adjusted under 35 U.S.C. 154(b) by 282 days.

This patent is subject to a terminal disclaimer.

(21) Appl. No.: 10/552,177

(22) PCT Filed: Apr. 16, 2004

(86) PCT No.: PCT/US2004/011982

§ 371 (c)(1),
(2), (4) Date: Nov. 20, 2006

(87) PCT Pub. No.: WO2004/093647

PCT Pub. Date: Nov. 4, 2004

(65) Prior Publication Data

US 2007/0178536 A1    Aug. 2, 2007

Related U.S. Application Data

(60) Provisional application No. 60/463,447, filed on Apr. 16, 2003.

(51) Int. Cl.
*G01N 33/00* (2006.01)

(52) U.S. Cl. .................. 435/7.24; 435/7.1; 435/7.21; 435/372; 435/287.2; 435/967; 435/973; 436/507; 436/520; 436/546; 436/548; 436/10; 436/63; 436/172; 436/811; 436/821

(58) Field of Classification Search ............. 435/7.1, 435/7.21, 7.23, 7.24, 7.25, 40.51, 337, 372, 435/287.2, 967, 973; 436/507, 520, 546, 436/548, 10, 63, 172, 811, 821; 422/61, 422/73
See application file for complete search history.

(56) References Cited

U.S. PATENT DOCUMENTS

| 7,361,517 B2 * | 4/2008 | Ahearn et al. ............... 435/7.21 |
| 7,390,631 B2 * | 6/2008 | Ahearn et al. ............... 435/7.25 |
| 2005/0037441 A1 | 2/2005 | Ahearn et al. |
| 2005/0042602 A1 * | 2/2005 | Ahearn et al. ............... 435/5 |
| 2007/0026387 A1 * | 2/2007 | Ahearn et al. ............... 435/5 |

FOREIGN PATENT DOCUMENTS

| WO | WO 94/10571 A1 | 5/1994 |
| WO | WO 03/022223 A2 | 3/2000 |

OTHER PUBLICATIONS

Buyon et al. Assessment of Disease Activity and Impending Flare in Patients with Systemic Lupus Erythematosus, Arthritis and Rheumatism, vol. 35, No. 9 (Sep. 1992).*
Freysdottir et al. A flow cytometric assay for measuring complement receptor 1 (CR1) and complement component C4d on erythrocytes, Journal of Immunological Methods 142: 45-52 (1991).*
Kuhne et al. Flow Cytometric Evaluation of Platelet Activation in Blood Collected Into EDTA vs. Diatube-H, American Journal of Hematology 50: 40-45 (1995).*
Sirois et al., An Enzyme-Linked Immunosorbent Assay for the Detection of Complement Components on Red Blood Cells, Am. Journ. Clin. Path. 82 (1): 67-73 (Jul. 1984).*
Senaldi, G., et al. Correlation of the activation of the fourth component of complement (C4) with disease activity in systemic lupus erythematosus, Ann. Rheum. Dis., 1988, vol. 47: 913-917).*
Alexander, Elaine, et al., "Serum complement activation in central nervous system disease in sjogren's syndrome;" The American Journal of Medicine, Oct. 1988, vol. 85, No. 4, abstract only.
Atkinson, J.P., et al., "Origin of the Fourth Component of Complement Related Chido and Rodgers Blood Group Antigens;" 1988; Compliment; vol. 5; pp. 65-76.
Bombardier, Claire, et al., "Derivation of the SLEDAI A Disease Activity Index for Lupus Patients;" Arthritis Rheum, Jun. 1992, vol. 35; No. 6; pp. 630-640.
Chudwin, D., et al., "Activation of the Alternative Complement Pathway by Red Blood Cells from Patients with Sickle Cell Disease;" Clinical Immunology and Immunopathology, May 1994, vol. 71, No. 2, pp. 199-202.

(Continued)

*Primary Examiner*—Gailene R Gabel
(74) *Attorney, Agent, or Firm*—Klarquist Sparkman, LLP (57) ABSTRACT

A method for identifying or monitoring SLE in an individual is provided. The method includes quantitating complement component C4d on the surfaces of platelets and comparing the amounts of C4d to reference levels of C4d on platelets of individuals without SLE and/or on platelets of the individual obtained at a different time. Kits for use in the above-described methods are provided along with computer readable media tangibly embodying executable instructions to perform the methods.

12 Claims, 1 Drawing Sheet

OTHER PUBLICATIONS

Corvetta, Angelo, et al.; "*Low Number of Complement C3b/C4b Receptors (CR1) on Erythrocytes from Patients with Essential Mixed Cryoglobulinemia, Systemic Lupus Erythematosus and Rheumatoid Arthritis: Relationship with Disease Activity, Anticardiolipin Antibodies, Complement Activation and Therapy*;" 1981, J. Rheumatol., vol. 18, pp. 1021-1025.

Cosio, F.G., et al., "*The high prevalence of severe early post-transplant renal allograft pathology in hepatitis C positive recipients;*" Transplantation, Oct. 27, 1996, vol. 62, No. 8, abstract only.

Freysdottir, Jona, et al.; "*A flow cytometric assay for measuring complement receptor 1 (CR1) and the complement fragments C3d and C4d on erythrocytes*;"1991, Journal of Immunological Methods, vol. 142, pp. 45-52.

Jouvin, Marie-Helene et al.; "*Decreased Expression of C3b Receptor (CR1) on Erythrocytes of Patients with Systemic Lupus erythematosus Contrasts with Its Normal Expression in Other Systemic Diseases and Does Not Correlate with the Occurrence or Severity of SLE Nephritis*;" Complement;1986, vol. 3, pp. 88-96.

Lach-Trifilieff, Estelle, et al., "*Complement Receptor 1 (CD35) on Human Reticulocytes: Normal Express in Systemic Lupus Erythematosus and HIV-Infected Patients*;" The Journal of Immunology, vol. 162, No. 12, Jun. 1999, pp. 7549-7554.

Lamprecht, P., et al., "*Immunological and clinical follow up of hepatitis C virus associated cryoglobulinaemic vasculitis*;" Annals of the Rheumatic Diseases, Apr. 2001, vol. 60, pp. 385-390.

Liang, Matthew H., et al., "*Reliability and Validity of Six Systems for the Clinical Assessment of Disease Activity in Systemic Lupus Erythematosus*," Arthritis Rheum, Sep. 1989, vol. 32; No. 9; pp. 1107-1118.

Manzi, Susan, et al.; "*Measurement of Erythrocyte C4d and Complement Receptor 1 in Systemic Lupus Erythematosus*;" Nov. 2004, Arthritis & Rheumatism, vol. 50, No. 11, pp. 3596-3604.

ACCN. No. 850463398 Medline. McCarthy, T., et al., "*Intrauterine devices and pelvic inflammatory disease*;" Australian and New Zealand Journal of Obstetrics and Gynecology, May 1984, vol. 24, No. 2, pp. 106-110, Abstract.

McGeer, P.L. et al.; "*Reactions of the Immune System in Chronic Degenerative Neurological Diseases*;" The Canadian Journal of Neurological Sciences; 1991, vol. 18; pp. 376-379.

ACCN. No. 90367342 Medline. Meliconi, R., et al., "*Complement activation products in idiopathic pulmonary fibrosis: relevance of fragment Ba to disease severity*;" Clinical Immunology and Immunopathology, Oct. 1990, vol. 57, No. 1, pp. 64-73, Abstract.

Ross, Gordon D. et al.; "*Disease-Associated Loss of Erythrocyte Complement Receptors (CR1, C3b Receptors) in Patients with Systemic Lupus Erythematosus and other Diseases Involving Auto antibodies and/or Complement Activation*;" 1985, Journal of Immunology, vol. 135, No. 3, pp. 2005-2014.

Sirois, M., et al., "*An Enzyme-linked Immunosorbent Assay for the Detection of Complement Components on Red Blood Cells*;" Am. Journ. Clin. Path., Jul. 1984, vol. 82, No. 1, pp. 67-73.

Tausk, Francisco, et al., "*The Expression of C3b Receptors in the Differentiation of Discoid Lupus Erythematosus and Systemic Lupus Erythematosus*;" Arthritis and Rheumatism, Jun. 1990, vol. 33, No. 6, pp. 888-892.

Tilley, C.A., et al., "*Localisation of Chido and Rodgers Determinants to the C4d Fragment of Human C4*;" Nature; Dec. 14, 1978; vol. 276; pp. 713-715.

Tsuboi, Y. et al.; "*Increased concentration of C4d complement protein in CSF in amyotrophic lateral sclerosis*"; Neurosurgery and Psychiatry 1994, vol. 57, pp. 859-861.

Yamada, T., et al. "*Complement-activated oligodendroglia: a new pathogenic entity identified by immunostaining with antibodies to human complement proteins C3d and C4d*;" Neuroscience Letters, 1990, vol. 112, pp. 161-166.

Buyon, JP, et al., "Assessment of disease activity and impending flare in patients with systemic lupus erythematosus," *Arthritis Rheum*, 1992, vol. 35, pp. 1028-1037.

Falk, RJ., et al., "Radioimmunoassay of the attack complex of complement in serum from patients with systemic lupus erythematosus,"*N. Engl. J. Med.*, 1985, vol. 312, pp. 1594-1599.

Manzi, S., et al., "Sensitivity and specificity of plasma and urine complement split products as indicators of lupus disease activity," *Arthritis & Rheumatism*, Jul. 1996, vol. 39, No. 7, pp. 1178-1188.

Manzi, S., et al., "New insights into complement: a mediator of injury and marker of disease activity in systemic lupus erthematosus," *Lupus*, 2004, vol. 13, pp. 1-6.

Navratil, JS, et al., "Apoptosis and autoimmunity: complement deficiency and systemic lupus erythematosus revisited," *Curr. Rheumatol. Rep.*, 2000, vol. 2, pp. 32-38.

Ricker, DM., et al., "Serum C3 levels are diagnostically more sensitive and specific for systemic lupus erythematosus activity than are serum C4 levels," The Lupus Nephritis Collaborative Study Group, *Am. J. Kidney Dis.*, 1991, vol. 18, pp. 678-685.

Senaldi, G., et al., "Correlation of the activation of the fourth component of complement (C4) with disease activity in systemic lupus erythematosus," *Ann. Rheum. Dis.*, 1988, vol. 47, pp. 913-917.

* cited by examiner

FIG. 1

IDENTIFICATION AND MONITORING OF SYSTEMIC LUPUS ERYTHEMATOSUS

CROSS-REFERENCES TO RELATED APPLICATIONS

This application is a U.S. National Phase Application, filed under 35 U.S.C. §371 of Patent Cooperation Treaty Application Number PCT/US2004/011982, filed Apr. 16, 2004, and claims the benefit of U.S. Provisional Application No. 60/463,447. Each of the aforementioned applications are hereby incorporated by reference in their entirety and for all purposes.

FIELD OF THE INVENTION

Identification and/or monitoring of patients with systemic lupus erythematosus, including methods and kits for carrying out this activity.

BACKGROUND OF THE INVENTION

Systemic lupus erythematosus (SLE) or lupus is the prototypic autoimmune disease resulting in multiorgan involvement. This anti-self response in SLE patients is characterized by autoantibodies directed against a variety of nuclear and cytoplasmic cellular components. These autoantibodies bind to their respective antigens, forming immune complexes that circulate and eventually deposit in tissues. This immune complex deposition causes chronic inflammation and tissue damage.

Both diagnosing and monitoring disease activity are problematic in patients with SLE. Diagnosis is problematic because the spectrum of disease is broad and ranges from subtle or vague symptoms to life-threatening multi-organ failure. There also are other diseases with multi-system involvement that can be mistaken for SLE, and vice versa. Criteria were developed for the purpose of disease classification in 1971 (Cohen, A S, et al., 1971, Preliminary criteria for the classification of systemic lupus erythematosus. *Bull Rheum Dis* 21:643-648) and revised in 1982 (Tan, E M, et al., 1982. The 1982 revised criteria for the classification of systemic lupus erythematosus. *Arth Rheum* 25:1271-1277.) and 1997 (Hochberg, M C. 1997. Updating the American College of Rheumatology revised criteria for the classification of systemic lupus erythematosus. *Arth Rheum* 40:1725). These criteria are meant to ensure that patients from different geographic locations are comparable. Of the 11 criteria, the presence of four or more, either serially or simultaneously, is sufficient for classification of a patient as having SLE. Although the criteria serve as useful reminders of those features that distinguish lupus from other related autoimmune diseases, they are unavoidably fallible. Determining the presence or absence of the criteria often requires interpretation. If liberal standards are applied for determining the presence or absence of a sign or symptom, one could easily diagnose a patient as having SLE when in fact they do not. Similarly, the range of clinical manifestations in SLE is much greater than that described by the eleven criteria and each manifestation can vary in the level of activity and severity from one patient to another. To further complicate a difficult diagnosis, symptoms of SLE continually evolve over the course of the disease. New symptoms in previously unaffected organs can develop over time. There is no definitive test for SLE and, thus, it is often misdiagnosed.

Monitoring disease activity also is problematic in caring for patients with SLE. Lupus progresses in a series of flares, or periods of acute illness, followed by remissions. The symptoms of a flare, which vary considerably between patients and even within the same patient, include malaise, fever, symmetric joint pain, and photosensitivity (development of rashes after brief sun exposure). Other symptoms of lupus include hair loss, ulcers of mucous membranes and inflammation of the lining of the heart and lungs, which leads to chest pain. Red blood cells, platelets and white blood cells can be targeted in lupus, resulting in anemia and bleeding problems. More seriously, immune complex deposition and chronic inflammation in the blood vessels can lead to kidney involvement and occasionally kidney failure, requiring dialysis or kidney transplantation. Since the blood vessel is a major target of the autoimmune response in lupus, premature strokes and heart disease are not uncommon. Over time, however, these flares can lead to irreversible organ damage. In order to minimize such damage, earlier and more accurate detection of disease flares would not only expedite appropriate treatment, but would reduce the frequency of unnecessary interventions. From an investigative standpoint, the ability to uniformly describe the "extent of inflammation" or activity of disease in individual organ systems or as a general measure is an invaluable research tool. Furthermore, a measure of disease activity can be used as a response variable in a therapeutic trial.

Two of the most commonly used instruments for SLE diagnosis are the Systemic Lupus Erythematosus Disease Activity Index (SLEDAI) (Bombardier, C., D. D. Gladman, et al. (1992). Derivation of the SLEDAI. A disease activity index for lupus patients. The Committee on Prognosis Studies in SLE. *Arth Rheum* 35: 630-40), and the Systemic Lupus Activity Measure (SLAM) (Liang, M. H., S. A. Socher, et al. (1989). Reliability and validity of six systems for the clinical assessment of disease activity in systemic lupus erythematosus. *Arth Rheum* 32: 1107-18). The SLEDAI includes 24 items, representing nine organ systems. The variables are obtained by history, physical examination and laboratory assessment. Each item is weighted from 1 to 8 based on the significance of the organ involved. For example, mouth ulcers are scored as 2, while seizures are scored as 8. The laboratory parameters that are included in the SLEDAI include white blood cell count, platelet count, urinalysis, serum C3, C4 and anti-dsDNA. The total maximum score is 105. The SLAM includes 32 items representing 11 organ systems. The items are scored not only as present/absent, but graded on a scale of 1 to 3 based on severity. The total possible score for the SLAM is 86. Both the SLEDAI and the SLAM have been shown to be valid, reliable, and sensitive to change over time (Liang, M. H., S. A. Socher, et al. (1989). Reliability and validity of six systems for the clinical assessment of disease activity in systemic lupus erythematosus. *Arth Rheum* 32:1107-18), and are widely used in research protocols and clinical trials. These indices are particularly useful for examining the value of newly proposed serologic or inflammatory markers of disease activity in SLE.

Despite the obvious utility of these instruments, there are some drawbacks. First, there is not always complete agreement between the SLAM and the SLEDAI in the same set of patients. There are several possible reasons for these discrepancies. Unlike the SLEDAI, the SLAM includes constitutional symptoms such as fatigue and fever, which may or may not be considered attributable to active SLE; this activity index relies on physician interpretation. In addition, the SLEDAI does not capture mild degrees of activity in some organ systems and does not have descriptors for several types of activity, such as hemolytic anemia. For these and other reasons, most studies incorporate more than one measure of disease activity. A general review of the state of the art can be found in Ramsey-Goldman, R. and Manzi, S. Systemic Lupus Erythematosus. In: Goldman and Hatch, Ed. Women and Health. Academic Press, San Diego, Calif. 2000: 704-723.

The complement system consists of a complex network of more than 30 functionally linked proteins that interact in a highly regulated manner to provide many of the effector functions of humoral immunity and inflammation, thereby serving as the major defense mechanism against bacterial and fungal infections. This system of proteins acts against invasion by foreign organisms via three distinct pathways: the classical pathway (in the presence of antibody) or the alternative pathway (in the absence of antibody) and the lectin pathway. Once activated, the proteins within each pathway form a cascade involving sequential self-assembly into multimolecular complexes that perform various functions intended to eradicate the foreign antigens that initiated the response.

The classical pathway is usually triggered by an antibody bound to a foreign particle. It consists of several components that are specific to the classical pathway and designated C1, C4, C2, (in that order in the pathway).

In the classical pathway, the first component C1q is bound to an antigen-antibody complex, activating the pathway. This event is followed by sequential activation of the two serine proteases C1r and C1s. Activated C1s has two substrates, the final two proteins of the classical pathway, namely C4 and C2. Protein C4 is cleaved into C4a and C4b. Protein C2 is cleaved to form C2a and C2b. Fragments C4b and C2a assemble to form C4b2a, which cleaves protein C3 into C3a and C3b, which completes activation of the classical pathway.

Fragments C4b and C3b are subject to further degradation by Factor I. This factor cleaves C4b to generate C4d and also cleaves C3b, to generate iC3b followed by C3d. Thus, activation of the classical pathway of complement can lead to deposition of a number of fragments, including C4d and iC3b on immune complexes or other activating surfaces. These fragments are ligands for complement receptor type 1 (CR1) on erythrocytes or red blood cells.

BRIEF SUMMARY OF THE INVENTION

It has been found that increased levels of complement C4d are present on the surfaces of platelets of individuals with systemic lupus erythematosis as compared to platelets obtained from healthy individuals. As shown herein, high levels of complement C4d associated with platelets correlates strongly with the presence of systemic lupus erythematosis in an individual and can be used for diagnosis and monitoring of systemic lupus erythematosis in the individual. The invention includes determining (quantitating) levels of complement C4d associated with platelets obtained from patients in which systemic lupus erythematosis is suspected or is present, and comparing those levels to those of platelets obtained from healthy individuals. In one embodiment, the amount of C4d associated with platelets is measured by detection of fluorescence by flow cytometry.

In one aspect, a method is provided for identifying systemic lupus erythematosus in an individual, comprising quantitating complement C4d associated with platelets obtained from the individual, and comparing the quantity of complement C4d associated with platelets obtained from the individual with quantities of complement C4d associated with platelets obtained from individuals not having systemic lupus erythematosus, wherein greater quantities of C4d associated with platelets obtained from the individual as compared to quantities of C4d associated with platelets obtained from individuals not having systemic lupus erythematosus correlates with the presence of systemic lupus erythematosus in the patient.

In another aspect, a method is provided for monitoring disease activity of systemic lupus erythematosus in an individual, comprising quantitating complement C4d associated with platelets obtained from the individual and comparing the quantity of complement C4d associated with platelets obtained from the individual with quantities of complement C4d associated with platelets obtained from either the individual at one or more different times or individuals not having systemic lupus erythematosus, wherein greater quantities of C4d associated with platelets obtained from the individual as compared to quantities of C4d associated with platelets obtained from either the individual at one or more different times or individuals not having systemic lupus erythematosus correlates with the presence of active systemic lupus erythematosus in the patient.

In still another aspect, a method is provided comprising quantitating complement C4d associated with platelets obtained from the individual and comparing the quantity of complement C4d associated with platelets obtained from the individual with quantities of complement C4d associated with platelets obtained from either the individual at one or more different times or individuals not having systemic lupus erythematosus, wherein greater quantities of C4d associated with platelets obtained from the individual as compared to quantities of C4d associated with platelets obtained from either the individual at one or more different times or individuals not having systemic lupus erythematosus correlates with the presence of systemic lupus erythematosus in the patient. In another embodiment a kit for use in identifying systemic lupus erythematosus in an individual, comprising a package containing a conjugate of an antibody specific for complement C4d with a first labeled moiety and instructions relating to use of the conjugate to identify complement C4d associated with platelets.

In yet another embodiment, a computer readable medium is provided, tangibly embodying executable instructions to perform a method, the method comprising: receiving data corresponding to a determination of complement component C4d deposited on surfaces of platelets; retrieving a reference value for complement component C4d deposited on surfaces of platelets of individuals; and comparing the data with the reference value.

Also provided is a computer readable medium tangibly embodying executable instructions to perform a method for identifying systemic lupus erythematosus in an individual, the method comprising: quantitating complement C4d associated with platelets obtained from the individual; and comparing the quantity of complement C4d associated with platelets obtained from the individual with quantities of complement C4d associated with platelets obtained from individuals not having systemic lupus erythematosus, wherein greater quantities of C4d associated with platelets obtained from the individual as compared to quantities of C4d associated with platelets obtained from individuals not having systemic lupus erythematosus correlates with the presence of systemic lupus erythematosus in the patient.

DETAILED DESCRIPTION OF THE INVENTION

The methods of this invention enable the identification and/or monitoring of SLE. Because this condition is a serious health problem, there is a need for relatively accurate and early diagnosis of this condition. Likewise, the ability to monitor the activity of this disease is of great importance. In the most general sense, the methods of this invention are based on the discovery by the inventors that a determination of C4d deposited on surfaces of platelets of a patient can serve as a diagnostic marker for SLE.

In diagnosing the occurrence, or previous occurrence, of SLE, complement component C4d deposited on surfaces of platelets in a sample is quantitated. The amount of C4d on the surfaces of the platelets is then compared with the quantities of C4d usually found on the surfaces of platelets of individuals not having SLE. For accuracy, the methods described herein measure C4d "associated with" platelets. The reason for this distinction arises form the fact that some methods, such as flow cytometry, measure C4d on the surface of intact platelets directly, while other methods quantitate surface C4d indirectly in a sample of disrupted platelets, and do not literally measure C4d on the surfaces of platelets. As such, as used herein, C4d is said to be "associated with" platelets, which means either C4d is on the surface of a platelet or it is present in a disrupted platelet sample, but in any case is either a direct or indirect measurement of C4d deposited on the surfaces of platelets.

In monitoring disease activity in a patient with SLE, the same determination is made in the patient's blood sample and is then compared with determinations of the quantities of C4d associated with platelets in a sample obtained from the same patient in the past.

In general, samples of blood are obtained from the patient and are treated with EDTA (ethylenediaminetetraacetate) to inhibit complement activation. The samples can be maintained at room temperature or under cold conditions. Assays preferably are run within 48 hours.

Complement C4d can be quantitated by a number of methods, including flow cytometry, ELISA using platelet lysates, and radioimmunoassay (RIA). In one embodiment, C4d is quantitated by flow cytometric methods, with measurements taken by direct or indirect immunofluorescence using polyclonal or monoclonal antibodies specific for C4d. Typically, the mean fluorescence channel (MFC) for platelet C4d is determined. Flow cytometry also may be used for monitoring disease activity in patients known to have SLE. In this method, anti-C4d antibody conjugated with a first fluorescent moiety is added to a blood sample. Preferably a platelet-specific antibody, conjugated with a second fluorescent moiety that is detectably different from the first fluorescent moiety, also is added to the blood sample to facilitate quantitation by cell sorting of C4d deposited on platelets and not on other blood components.

Kits for use in conducting flow cytometric assays for both the diagnosing of disease and monitoring of disease activity are also provided. Kits may include, in a package, any of the various reagents needed to perform the methods described herein. For example, for immunofluorescence assays, the kits generally will comprise a conjugate of an antibody specific for complement component C4d with a labeled moiety, such as a fluorescent moiety, and preferably also a conjugate of a platelet-specific antibody with a different fluorescent moiety, for example and without limitation, a monoclonal antibody specific for platelet CD42b. The antibody or antibodies typically are monoclonal. Additionally, the kits will comprise such other material as may be needed in carrying out assays of this type, for example and without limitation: buffers; radiolabeled antibodies, secondary antibodies, as in the case of ELISA or RIA assays, that are conjugated with a labeling moiety or other tag, such as avidin or biotin, further conjugated with a fluorochrome or enzyme such as alkaline phosphatase or peroxidase; colorimeter reagents and instructions for use of the anti-C4d antibody and/or other components of the kit, to quantitate C4d levels on platelets.

Antibodies useful in the described methods and kits are known. Hybridomas secreting Anti-CD42b antibodies are available, for example and without limitation, from Becton Dickinson Immunocytometry Systems, San Jose, Calif. Anti-C4d antibodies are available from Quidel Corp. in San Diego, Calif. (#A213) and are generally described in Rogers, J., N. Cooper, et al. Complement activation by beta-amyloid in Alzheimer's disease. *PNAS* 89:10016-10020, 1992; Schwab, C., et al. Neurofibrillary tangles of Guam Parkinson-dementia are associated with reactive microglia and complement proteins. *Brain Res* 707(2):196 1996; Gemmell, C. A flow cytometric immunoassay to quantify adsorption of complement activation products on artificial surfaces. *J Biomed Mater Res* 37:474-480, 1997; and, Stoltzner, S. E., et al. Temporal accrual of complement proteins in amyloid plaques in patients with Down's syndrome with Alzheimer's disease. *Am J Path* 156:489-499, 2000. Binding reagents specific to C4d and/or CD42b, including, without limitation, Fv Fragments, single chain Fv Fragments, Fab fragments, F(ab)2 fragments or multivalent binding reagents, are understood as synonymous with "antibodies" or "antibody".

The determination of the C4d and CD42b values alternatively may be conducted using a number of standard measurement techniques such as ELISA or RIA. Instead of fluorescent labels, used for flow cytometry, there may be used labels of other types, such as radioactive and colorimetric labels. If such other types of assays are to be used, the kits will comprise antibodies, typically monoclonal antibodies, specific for C4d and CD42b conjugated with appropriate labels such as radioactive iodine, avidin, biotin or enzymes such as alkaline phosphatase or peroxidase.

Diagnosis of a patient with SLE is carried out by comparing the determination of C4d with a base value or range of values for the quantities of C4d typically present on the surfaces of platelets in normal individuals. In normal individuals, C4d is not present at detectable levels. When using flow cytometric measurement with indirect immunofluorescence, the MFC of C4d on platelets of healthy individuals ranges from −1.17 to 0.87 (mean −0.39). (Table I and Table IV). The MFC of platelet C4d in patients having SLE was higher than that of healthy individuals and ranged from −0.85 to 31.67 (mean 2.65). (Table II and Table IV).

A particular feature of the methods of this invention is to indicate or reflect SLE activity that has occurred in the patient during the preceding several weeks or even several months. It is possible, using this procedure, to identify the occurrence of a flare-up of SLE during the previous few weeks or possibly even the previous several months due to persistence of C4d deposited on the surface of platelets.

Automation and Computer Software

The determinations of C4d and the diagnostic and disease activity monitoring methods described above can be carried out manually, but often are conveniently carried out using an automated system and/or equipment in which the blood sample is analyzed automatically to make the necessary determination or determinations, and the comparison with the base or reference value is carried out automatically, using computer software appropriate to that purpose.

Thus, in one aspect, the invention comprises a method for diagnosing or monitoring systemic lupus erythematosus in an individual comprising (a) automatically determining, in a blood sample from the individual containing platelets, complement component C4d deposited on surfaces of platelets in the sample, and (b) automatically comparing said determinations with reference values for component C4d on surfaces of platelets.

Figure 1:
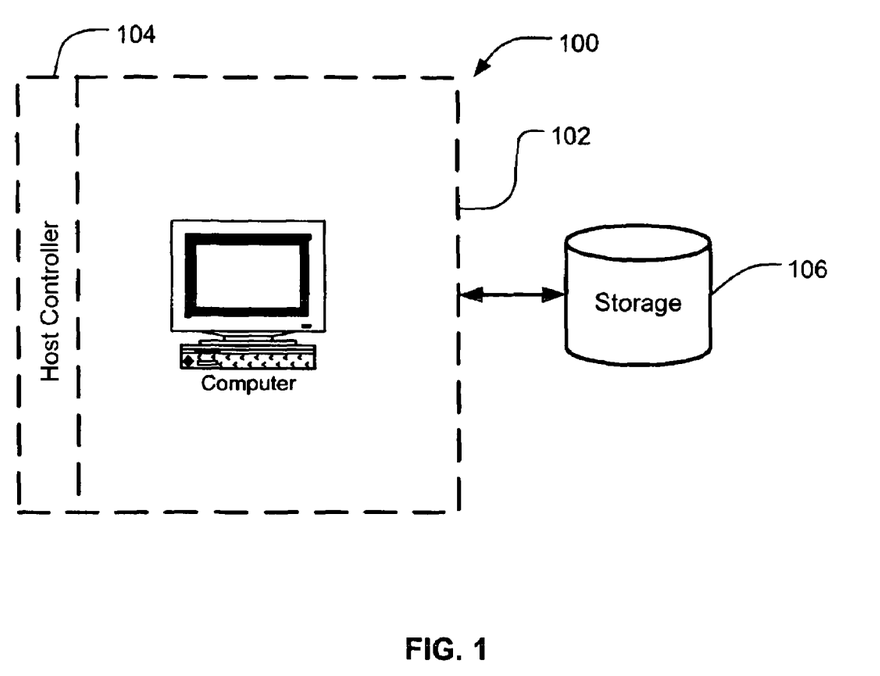

In reference to FIG. 1, one embodiment of the present invention comprises a system 100, which may include a device 102 operating under the command of a controller 104. The broken lines are intended to indicate that in some implementations, the controller 104, or portions thereof considered collectively, may instruct one or more elements of the device 102 to operate as described. Accordingly, the functions described herein may be implemented as software executing in the system 100 and controlling one or more elements thereof. An example of a device 102 in accordance with one embodiment of the present invention is a general-purpose computer capable of responding to and executing instructions in a defined manner. Other examples include a special-purpose computer including, for example, a personal computer (PC), a workstation, a server, a laptop computer, a web-enabled telephone, a web-enabled personal digital assistant (PDA), a microprocessor, an integrated circuit, an application-specific integrated circuit, a microprocessor, a microcontroller, a network server, a Java virtual machine, a logic array, a programmable logic array, a micro-computer, a mini-computer, or a large frame computer, or any other component, machine, tool, equipment, or some combination thereof capable of responding to and executing instructions. Furthermore, the system 100 may include a central processing engine including a baseline processor, memory, and communications capabilities. The system 100 also may include a communications system bus to enable multiple processors to communicate with each other. In addition, the system 100 may include a storage 106 in the form of a disk drive, cartridge drive, and control elements for loading new software. In embodiments of the invention, one or more reference values may be stored in a memory associated with the device 102. After data corresponding to a determination of complement C4d is obtained (e.g., from an appropriate analytical instrument), the device 102 may compare the C4d data with one or more appropriate reference values. After this comparison takes place, the device 102 can automatically determine if the data corresponding to the determination of complement C4d is associated with SLE.

Embodiments of the controller 104 may include, for example, a program, code, a set of instructions, or some combination thereof, executable by the device 102 for independently or collectively instructing the device 102 to interact and operate as programmed. One example of a controller 104 is a software application (e.g., operating system, browser application, client application, server application, proxy application, on-line service provider application, and/or private network application) installed on the device 102 for directing execution of instructions. In one embodiment, the controller 104 may be a Windows™ based operating system. The controller 104 may be implemented by utilizing any suitable computer language (e.g., C\C++, UNIX SHELL SCRIPT, PERL, JAVA, JAVASCRIPT, HTML/DHTML/XML, FLASH, WINDOWS NT, UNIX/LINUX, APACHE, RDBMS including ORACLE, INFORMIX, and MySQL) and/or object-oriented techniques.

In one embodiment, the controller 104 may be embodied permanently or temporarily in any type of machine, component, physical or virtual equipment, storage medium, or propagated signal capable of delivering instructions to the device 102. In particular, the controller 104 (e.g., software application and/or computer program) may be stored on any suitable computer readable media (e.g., disk, device, or propagated signal), readable by the device 102, such that if the device 102 reads the storage medium, the functions described herein are performed. For example, in one embodiment, the controller 104 may be embodied in various computer-readable media for performing the function of:

(a) receiving data corresponding to a determination of complement component C4d deposited on surfaces of platelets;

(b) retrieving a reference value for complement component C4d deposited on surfaces of platelets of individuals; and (c) comparing the data in (a) with the reference value of (b).

All publications and patent applications cited in this specification are herein incorporated by reference as if each individual publication or patent application were specifically and individually indicated to be incorporated by reference.

EXAMPLES AND EXPERIMENTAL DATA

The following examples are provided by way of illustration only and not by way of limitation. Those of skill will readily recognize a variety of noncritical parameters that could be changed or modified to yield essentially similar results.

Example 1

Assays of Platelet C4d in Healthy Controls: Negative

Twenty-five healthy individuals were studied. As shown in Table I, C4d was not detected on platelets of each of the twenty-five healthy individuals. Samples of 1 mL of EDTA-anticoagulated peripheral blood were taken from each individual and used as a source of platelets. The platelets were washed and resuspended in Fluorescence-Activated Cell Sorter (FACS) buffer. Levels of C4d and CD42b were measured by two color indirect immunofluorescence using monoclonal antibodies specific for C4d and CD42b, respectively. Levels of C4d and CD42b are quantitated by Flow cytometry using a FACSCalibur cytometer (Becton Dickinson). The platelets were identified by forward and side scatter and CD42b-fluorescence, and the mean fluorescence channel (MFC) was determined for C4d.

More particularly, blood was drawn into 4 cc Vacutainer tubes containing 7.2 mg EDTA as an anticoagulant (Becton Dickinson, Franklin Lakes, N.J.), and processed within two hours. Whole blood was diluted 1/10 in phosphate buffered saline (PBS). 10 µl aliquots of the diluted blood were immunofluorescently labeled for flow cytometry with 0.25 µg of PE-labeled anti-CD42b monoclonal antibody (Becton Dickinson Immunocytometry Systems, San Jose, Calif.) to identify platelets, and 0.25 µg of one of the following monoclonal antibodies conjugated to Alexa Fluor 488 (Molecular Probes, Eugene, Oreg.): anti-C4d (Quidel Corp., San Diego, Calif.) or the isotype control MOPC21. Samples were incubated 10 min at room temperature, then diluted with 0.5 ml cold PBS and analyzed on a FACSCalibur flow cytometer (Becton Dickinson Immunocytometry Systems, San Jose, Calif.). Platelets were electronically gated by forward scatter properties and expression of CD42b, a platelet-specific marker. Nonspecific binding of immunoglobulins to platelets was determined by performing identical assays in parallel using the isotype control antibody MOPC21 (obtained from American Type Culture Collection, Manassas, Va.). Specific binding of anti-C4d and anti-CD42b were determined by subtracting the MFC obtained with MOPC21 from the MFC obtained with anti-C4d and anti-CD42b, respectively.

Example 2

Assays of Platelet C4d to Distinguish Patients with SLE from Healthy Controls This example describes conducting assays on patients to diagnose systemic lupus erythematosus, and to establish reference values or ranges of values for complement component C4d.

For this purpose, we recruited 115 patients with lupus from our outpatient office. A single determination platelet C4d was made in 115 individuals who met ACR criteria for the diagnosis of SLE (Table II) and in 35 healthy controls (Table I). The mean and median values of CR1 and C4d for patients with SLE and healthy controls are shown in Table IV. Whereas the mean value for C4d in healthy individuals was −0.39, the mean value for C4d among patients with SLE was 2.65 (p=0.0001).

TABLE I

| Healthy Controls (n = 25) Mean MFC = −0.39 Range (−1.17)-(+0.87) | |
|---|---|
| Platelet C4d | MFC |
| 2003 | −0.28 |
| 2005 | −0.23 |
| 2006 | −0.51 |
| 2007 | −0.05 |
| 2008 | 0.20 |
| 2009 | 0.15 |
| 2010 | −0.39 |
| 2011 | −0.71 |
| 2013 | −0.96 |
| 2017 | 0.87 |
| 2020 | −0.29 |
| 2021 | −0.56 |
| 2022 | 0.38 |
| 2025 | −0.73 |
| 2026 | −0.24 |
| 2027 | −0.34 |
| 2028 | −0.74 |
| 2029 | −0.05 |
| 2030 | −0.51 |
| 2031 | −1.03 |
| 2032 | −0.42 |
| 2034 | −0.71 |
| 2035 | −0.86 |
| 2036 | −0.48 |
| 2037 | −1.17 |

TABLE II

| SLE Patients (n = 115) MEAN = 2.65 RANGE = (−0.85)-(+31.67) | |
|---|---|
| Patient ID | Platelet C4d |
| 1001 | 3.79 |
| 1002 | 0.59 |
| 1003 | 1.36 |
| 1006 | 4.64 |
| 1008 | 0.00 |
| 1009 | 4.58 |
| 1010 | 20.82 |
| 1011 | 0.74 |
| 1012 | 1.47 |
| 1013 | 10.37 |
| 1014 | −0.40 |
| 1015 | 9.44 |
| 1016 | 4.18 |
| 1017 | 1.05 |
| 1018 | 1.37 |
| 1019 | 0.00 |
| 1021 | 0.92 |
| 1027 | 0.00 |
| 1030 | 2.36 |
| 1031 | 2.76 |
| 1032 | 0.38 |
| 1034 | 0.00 |
| 1035 | 0.14 |
| 1036 | 7.11 |
| 1037 | 0.00 |
| 1038 | 0.70 |
| 1039 | 12.60 |
| 1043 | 0.00 |
| 1044 | 0.94 |
| 1045 | 0.00 |
| 1046 | 0.40 |
| 1047 | 1.52 |
| 1048 | 0.00 |
| 1050 | 3.80 |
| 1052 | 5.92 |
| 1053 | 1.11 |
| 1055 | 1.24 |
| 1056 | 14.90 |
| 1057 | 0.00 |
| 1059 | 0.03 |
| 1060 | 0.00 |
| 1061 | 4.41 |
| 1063 | 0.84 |
| 1064 | −0.15 |
| 1066 | 31.67 |
| 1067 | 0.18 |
| 1068 | 2.63 |
| 1071 | 0.03 |
| 1072 | 0.00 |
| 1073 | 1.61 |
| 1074 | 0.02 |
| 1075 | 23.61 |
| 1076 | 8.60 |
| 1078 | −0.17 |
| 1079 | 1.61 |
| 1080 | 2.59 |
| 1081 | 6.59 |
| 1082 | 2.52 |
| 1083 | 0.05 |
| 1084 | 0.06 |
| 1085 | 4.48 |
| 1086 | −0.06 |
| 1087 | 0.58 |
| 1089 | −0.10 |
| 1090 | 9.71 |
| 1091 | −0.14 |
| 1092 | −0.38 |
| 1093 | 0.34 |
| 1094 | −0.53 |
| 1095 | −0.11 |
| 1096 | −0.85 |
| 1097 | −0.12 |
| 1098 | −0.24 |
| 1099 | −0.31 |
| 1100 | 0.52 |
| 1101 | 1.49 |
| 1102 | 8.74 |
| 1103 | −0.35 |
| 1104 | −0.22 |
| 1105 | −0.31 |
| 1106 | 0.90 |
| 1108 | 0.89 |
| 1109 | 1.06 |
| 1110 | 2.69 |

TABLE II-continued

SLE Patients (n = 115)
MEAN = 2.65 RANGE = (−0.85)-(+31.67)

| Patient ID | Platelet C4d |
|---|---|
| 1111 | 0.59 |
| 1112 | 1.53 |
| 1113 | 1.03 |
| 1115 | 0.92 |
| 1116 | 2.16 |
| 1117 | 1.26 |
| 1118 | 4.97 |
| 1119 | 0.62 |
| 1120 | 0.94 |
| 1121 | 6.17 |
| 1122 | 3.75 |
| 1123 | 1.78 |
| 1124 | 1.20 |
| 1125 | 3.10 |
| 1126 | 2.57 |
| 1127 | 1.47 |
| 1128 | 1.67 |
| 1129 | 1.29 |
| 1130 | 6.35 |
| 1131 | 2.36 |
| 1132 | 7.25 |
| 1134 | 1.47 |
| 1135 | 0.86 |
| 1136 | 1.70 |
| 1137 | 2.70 |
| 1138 | 0.92 |
| 1139 | 1.30 |
| 1140 | 1.34 |
| 1141 | 1.09 |
| 1142 | 3.82 |
| 1143 | 1.60 |

In SLE patients compared to healthy controls, the sensitivity and specificity of these measures were 39% and 100%, respectively (Table V).

Example 3

Assay of Platelet C4d for Distinguishing Patients with SLE from Patients with Other Diseases These studies of patients with SLE vs. healthy controls were followed by studies to compare patients with SLE with patients diagnosed with diseases other than SLE (n=103). For this comparison, we studied patients with systemic sclerosis (n=13), rheumatoid arthritis (n=17), osteoarthritis (n=2), hepatitis C virus infection (n=14), polymyositis/dermatomyositis (n=8), Sjogren's syndrome (n=2), urticarial vasculitis (n=1), sickle cell anemia (n=8), overlap syndrome/undifferentiated connective tissue disease (n=12), leukemia/lymphoma (n=9), primary Raynaud's syndrome (n=3), hemophilia (n=2), and psoriatic arthritis (n=2). A single determination of platelet C4d was made using the same assay. The mean and median values of C4d for patients with SLE, as compared with patients with other diseases, are shown in Table IV. Whereas the mean value for C4d in patients with other diseases was 0.53, the mean value for C4d among patients with SLE was 2.59 (p=0.0001). In SLE patients compared to patients with other diseases, the sensitivity and specificity of these measures were 39% and 94%, respectively (Table V).

TABLE III

Other Diseases (n = 103)
MEAN = 0.68 RANGE = (−3.29)-(+10.22)

| Patient ID | Platelet C4d |
|---|---|
| 3003 | 1.11 |
| 3004 | 0.42 |
| 3014 | 0.66 |
| 3021 | 0.17 |
| 3022 | 0.28 |
| 3023 | 0.00 |
| 3028 | 0.56 |
| 3029 | 0.53 |
| 3030 | 1.03 |
| 3031 | 10.22 |
| 3034 | 1.02 |
| 3035 | 1.15 |
| 3036 | 1.33 |
| 4001 | 0.08 |
| 4002 | 0.73 |
| 4008 | 0.91 |
| 4011 | 1.07 |
| 4018 | 0.02 |
| 4019 | 1.04 |
| 4020 | 0.20 |
| 4021 | 0.44 |
| 4022 | 0.10 |
| 4023 | 1.17 |
| 4024 | 0.03 |
| 4025 | 0.28 |
| 4026 | 0.32 |
| 4027 | 0.06 |
| 4028 | 1.22 |
| 4030 | 0.53 |
| 4033 | 1.03 |
| 4034 | 1.15 |
| 5001 | 1.05 |
| 5003 | 0.55 |
| 6001 | 2.12 |
| 6002 | 1.04 |
| 6003 | 0.47 |
| 6004 | 0.50 |
| 6005 | 0.04 |
| 6006 | 0.40 |
| 6007 | 0.04 |
| 6008 | 0.18 |
| 6009 | 0.11 |
| 6010 | 3.58 |
| 6011 | 0.14 |
| 6012 | 0.40 |
| 6013 | 0.71 |
| 6014 | 0.21 |
| 6015 | 1.28 |
| 6016 | 1.01 |
| 6017 | 2.00 |
| 8001 | 0.54 |
| 8002 | 1.46 |
| 8003 | 0.05 |
| 8004 | 1.39 |
| 8005 | 1.83 |
| 8007 | 0.03 |
| 8008 | 0.02 |
| 8009 | 0.10 |
| 8012 | 0.29 |
| 8013 | 0.34 |
| 8015 | 0.56 |
| 8018 | 0.24 |
| 8019 | 0.05 |
| 8020 | 0.25 |
| 10001 | 0.89 |
| 12001 | 0.29 |
| 12002 | 0.06 |
| 12003 | 0.16 |
| 12004 | 0.46 |
| 12005 | 0.33 |
| 12006 | 0.05 |
| 12007 | 0.14 |
| 12008 | 0.10 |
| 13003 | 1.37 |
| 13007 | 0.46 |
| 13008 | 0.08 |

| | |
|---|---|
| 13009 | 0.47 |
| 13010 | 0.13 |
| 13011 | 1.45 |
| 13012 | 0.15 |
| 13013 | 0.42 |
| 13014 | 0.20 |
| 13015 | 1.04 |
| 13016 | 0.97 |
| 13017 | 0.58 |
| 14001 | 1.15 |
| 14002 | 1.63 |
| 14003 | 0.52 |
| 14004 | 0.67 |
| 14005 | 1.25 |
| 14006 | 1.47 |
| 14007 | 0.17 |
| 14008 | 0.14 |
| 14009 | 0.05 |
| 15002 | 0.11 |
| 15003 | 0.40 |
| 15004 | 0.89 |
| 16001 | 1.06 |
| 16002 | 0.14 |
| 17001 | −3.29 |
| 17002 | 0.17 |
| 18001 | 0.80 |
| 18002 | 1.00 |

Example 4

Assays of CR1 and C4d for Measuring Disease Activity in Patients with SLE

We then examined the utility of platelet C4d levels in measuring disease activity as defined by the Systemic Lupus Erythematosus Disease Activity Index (SLEDAI). We present the results of the first 115 lupus patients entered into the study. Using a univariate linear regression model, platelet C4d was the most significant predictor of disease activity ($p=0.002$).

TABLE IV

Analysis of Platelet C4d
Platelet-C4d

| | | Mean | Standard Deviation | Median |
|---|---|---|---|---|
| SLE | (n = 15) | 2.65 | 4.76 | 2.13 |
| Healthy Controls | (n = 25) | −0.39 | 0.46 | −0.42 |
| Other Diseases | (n = 103) | 0.68 | 1.18 | 0.46 |

| Comparison | C4 (p values) |
|---|---|
| SLE vs. Healthy Controls | 0.0001 |
| SLE vs. Other Diseases | 0.0001 |

TABLE V

Analysis of Platelet C4d

| Comparison | Sensitivity | Specificity |
|---|---|---|
| SLE vs. Healthy Control | .39 | 1.00 |
| SLE vs. Other Diseases | .39 | .94 |

Although the foregoing invention has been described in some detail by way of illustration and example for purposes of clarity of understanding, it will be readily apparent to those of ordinary skill in the art in light of the techniques of this invention that certain changes and modifications may be made thereto without departing from the spirit or scope of the appended claims.

We claim:

1. A method for identifying systemic lupus erythematosus in an individual, the method comprising:
   quantitating complement C4d associated with platelets obtained from a platelet sample of the individual; and
   comparing the quantity of complement C4d associated with platelets obtained from the platelet sample of the individual with quantities of complement C4d associated with platelets obtained from platelet samples of individuals not having systemic lupus erythematosus;
   wherein the quantities of C4d associated with platelets obtained from the platelet sample of the individual being higher as compared to quantities of C4d associated with platelets obtained from the platelet samples of individuals not having systemic lupus erythematosus correlates with the presence of systemic lupus erythematosus in the patient.

2. The method of claim 1, further comprising quantitating CD42b associated with platelets obtained from the platelet sample of the individual.

3. The method of claim 1, wherein quantitation of complement C4d is conducted by a method comprising binding the C4d to a conjugate of an antibody specific for complement C4d with a first labeled moiety and quantitating the first labeled moiety.

4. The method of claim 3, wherein the first labeled moiety is a fluorescent moiety.

5. The method of claim 4, wherein the first fluorescent moiety is quantitated by flow cytometric analysis.

6. The method of claim 3, further comprising binding CD42b to a conjugate of an antibody specific for CD42b with a second labeled moiety that is detectably different from the first labeled moiety, and quantitating the second labeled moiety.

7. The method of claim 6, wherein the second labeled moiety is a fluorescent moiety.

8. The method of claim 7, wherein the second fluorescent moiety is quantitated by flow cytometric analysis.

9. A method of monitoring disease activity of systemic lupus erythematosus in an individual comprising:
   quantitating complement C4d associated with platelets obtained from a platelet sample of the individual; and
   comparing the quantity of complement C4d associated with platelets obtained from the platelet sample of the individual with quantities of complement C4d associated with platelets obtained from either the platelet sample of the individual at one or more different times or platelet samples of individuals not having systemic lupus erythematosus;
   wherein the quantities of C4d associated with platelets obtained from the platelet sample of the individual being higher as compared to quantities of C4d associated with platelets obtained from platelet samples of individuals not having systemic lupus erythematosus correlates with the presence of systemic lupus erythematosus in the patient.

10. A kit for use in identifying systemic lupus erythematosus in an individual, comprising a package containing a conjugate of an antibody specific for complement C4d with a first labeled moiety and instructions relating to use of the conjugate to identify complement C4d associated with platelets and a conjugate of an antibody specific for CD42b with a second labeled moiety that is detectably different from the first labeled moiety.

11. The kit of claim 10, wherein the first labeled moiety is a fluorescent moiety.

12. The kit of claim 11, wherein the second labeled moiety is a fluorescent moiety.

* * * * *

UNITED STATES PATENT AND TRADEMARK OFFICE
CERTIFICATE OF CORRECTION

| | | |
|---|---|---|
| PATENT NO. | : 7,588,905 B2 | Page 1 of 1 |
| APPLICATION NO. | : 10/552177 | |
| DATED | : September 15, 2009 | |
| INVENTOR(S) | : Ahearn et al. | |

It is certified that error appears in the above-identified patent and that said Letters Patent is hereby corrected as shown below:

<u>In the Specification:</u>

Insert in Column 1, line 14, --This invention was made with government support under grant numbers RO1HL-074335, K23 AR-051044, RO1AR-4676402 and RO1AR-46588, awarded by the National Institutes of Health, and grant numbers K24 AR-02213 and MO1-RR-00056, awarded by the National Center for Research Resources. The government has certain rights in the invention--.

Signed and Sealed this
Fourth Day of February, 2014

Michelle K. Lee
*Deputy Director of the United States Patent and Trademark Office*